United States Patent
Nowakowski

[11] Patent Number: 6,159,232
[45] Date of Patent: Dec. 12, 2000

[54] CLOTTING CASCADE INITIATING APPARATUS AND METHODS OF USE AND METHODS OF CLOSING WOUNDS

[75] Inventor: Karol L. Nowakowski, Circle Pines, Minn.

[73] Assignee: Closys Corporation, Minneapolis, Minn.

[21] Appl. No.: 09/212,080

[22] Filed: Dec. 15, 1998

[51] Int. Cl.[7] .................................................. A61B 17/12
[52] U.S. Cl. .......................................... 606/213; 606/214
[58] Field of Search ................................... 606/213, 214; 604/11, 19, 60

[56] References Cited

U.S. PATENT DOCUMENTS

| | | | |
|---|---|---|---|
| 3,223,083 | 12/1965 | Cobey | 606/214 |
| 5,318,524 | 6/1994 | Morse et al. | 606/214 |
| 5,383,896 | 1/1995 | Gershony et al. | 606/213 |
| 5,510,102 | 4/1996 | Cochrum | |
| 5,585,007 | 12/1996 | Antanavich et al. | |
| 5,674,394 | 10/1997 | Whitmore | 210/321.6 |
| 5,676,689 | 10/1997 | Kensey et al. | 606/213 |
| 5,741,223 | 4/1998 | Janzen et al. | 604/15 |
| 5,788,662 | 8/1998 | Antanavich et al. | |
| 5,795,571 | 8/1998 | Cederholm-Williams et al. | |
| 5,814,066 | 9/1998 | Spotnitz | 606/214 |
| 5,957,952 | 9/1999 | Gershony et al. | 606/213 |

FOREIGN PATENT DOCUMENTS 406181979  7/1994  Japan ..................... 606/214

OTHER PUBLICATIONS

Effect of Delay and Storage on Whole–Blood Clotting Analysis as Determined by Thrombelatography, J. Clinical Monitoring, 1993, vol. 9, p. 5–8.

*Primary Examiner*—Gary Jackson
*Attorney, Agent, or Firm*—Moore & Hansen

[57] ABSTRACT

Wound closure methods and apparatus are provided which utilize blood fluid by activating the clotting cascade of the blood fluid outside the body within a substantially enclosed sterile container then introducing the blood fluid to the wound site to complete clotting. Methods and apparatus for providing ways of inhibiting anticoagulants and slowing fibrin clot degradation are also disclosed. Kits for practicing the invention singularly or in combination with and/or associated with preferred procedures are also disclosed.

60 Claims, 4 Drawing Sheets

# CLOTTING CASCADE INITIATING APPARATUS AND METHODS OF USE AND METHODS OF CLOSING WOUNDS

BACKGROUND OF THE INVENTION

1. Field of Invention

This invention concerns novel methods and apparatus for medical applications, specifically wound closure applications. More particularly, the invention manipulates blood fluids, or its components, in new ways to close tissue or vascular wounds.

2. Background Information

Numerous medical applications exist where sealing of biological tissue is desired. U.S. Pat. No. 5,510,102 to Cochrum identifies many of these including trauma of liver, spleen, pancreas, lung, bone, etc., cardiovascular and vascular, such as microvascular anastomoses, vascular grafts, intraoperative bleeding, and aortic repair, for thoracic IS surgery such as lung biopsy, for transplant of heart, renal, pancreas, lung, bone or bone marrow, for neurosurgery such as nerve anastomoses, or CSF leak repair, for endoscopic surgery, such as hemostasis in hepatic trauma, or bile duct repair, for interventional radiology, such as hemostasis for percutaneous liver biopsy or vascular occlusion, for gastrointestinal surgery such as colonic anastomoses, for obstetrics and gynecology such as rectovaginal fistulas, for pediatric and fetal surgery, for plastic surgery and burn repairs such as grafting process of cultured epidermis, for dermatology such as hair transplants, for dental surgery, for ophthalmic cataract surgery, for urology, for correction of urinary fistulas and such others. With such broad application of the present invention possible, one use is selected for method and apparatus illustrative continuity purposes throughout this document. The selected application is sealing of a vascular wound resulting from percutaneous entry as is frequently done in the performance of angiography, angioplasty, and atherectomy procedures.

Percutaneous vascular access is typically done in the context of performing some minimally invasive surgical procedure. Minimally invasive techniques are used to reduce trauma to the patient. Reduced trauma typically translates to improved patient comfort, less procedural complications, and lower costs. The vessel accessed is typically the femoral or radial artery. Access involves placement of an introducer's distal tip beneath the patient's skin and through the arterial wall. To the extent possible, percutaneous access preserves the integrity of tissue covering the artery. As a result, when the introducer is to be removed the arterial access site is not exposed and the arterial wound is preferably closed without cutting down through the overlaying tissue to expose the site.

To accomplish hemostasis at the wound, numerous methods of post-introducer arterial closure have been invented. Most of these are similar to each other in many respects with some novel differentiating characteristic separating them. Many of them rely upon the clotting cascades being initiated at the wound site. Many prior art devices may be broadly classified into two groups those that passively support onset of the clotting cascades at the wound site and those that actively cause the clotting cascades at the wound site. By example, mechanical methods of holding the wound closed by clamping or suturing to prevent hemorrhaging are passive methods because they merely prevent continual flushing of the site as the clot attempts to take hold. To a lesser degree the body also does this naturally by vascular constriction. The second grouping—active clotting at the wound site— includes those methods which place a clot inducing material at the wound site. Such clot inducing formulations are many and typically either supply thrombin directly or potentially stimulate thrombin release at the wound site.

Disadvantages of the prior art vary based on the method employed. Generally speaking, passive devices like clamping or suturing are generally complex and/or expensive. Clamping for example can be labor intensive to administer manually and is uncomfortable for the patient by any means. Suturing on the other hand is complex and expensive because the wound site is typically small, remote, and blind to the physician placing the suture. Active devices are often costly and potentially dangerous. Active devices typically require placement of a clot-inducing foreign material in the patient which necessitates either expensive pretesting for potential allergic reactions or accepting the occasional adverse reaction which could lead to anaphylactic shock and even death as reported in *J. Trauma,* 31:408 (1991). Transmission of infectious diseases can occur when the material used was manufactured from pooled human blood as reported in *Opth. Surg.,* 23:640 (1992). Autologous preparations like fibrin glue as described in U.S. Pat. No. 5,674, 394 to Whitmore are well known but significant preparation with the associated labor and material costs are required and typically an additional thrombin material must still be added at the wound site.

Despite the need for a device and method which overcomes the limitations of the prior art, none insofar as is known has been proposed or developed until the present invention.

Accordingly, it will be appreciated that there is a need for an efficient way of closing wounds. The present inventions provide advantages over the prior devices and the prior methods used to close wounds, and also offers other advantages over the prior art and solves other problems associated therewith.

SUMMARY OF THE INVENTION

This present invention provides methods of closing a wound including the steps of treating a blood fluid such that the clotting cascade is initiated and transporting the treated blood fluid to the wound to form a clot at the wound thereby preventing fluid from passing through the wound. The invention further provides the clotting cascade initiation apparatus including a clotting cascade initiation apparatus within which a blood fluid can be received, the blood fluid being useful for treatment of a wound within a patient, said apparatus including a substantially enclosed sterile containment chamber within which the blood fluid can be received and retained, and a procoagulating agent within the substantially enclosed sterile containment chamber wherein a clotting cascade can be initiated when the blood fluid is accepted in to the sterile containment chamber and exposed to the wound within the patient subsequent to the initiation of the clotting cascade such that the clotting cascade can be completed and a clot can form within the wound. The invention further provides the method of using a clotting cascade initiation apparatus including a step of providing a mechanism to substantially neutralize an anticoagulant. The invention further provides the method of using a clotting cascade initiation apparatus including a step of providing a mechanism to substantially neutralize an anticlot. The invention further provides the method of using a clotting cascade initiation apparatus including providing a kit to conveniently practice the method.

It is believed that the present invention offers significant advantages over the prior art methods and apparatuses. By activating the blood fluid clotting cascade within a substantially enclosed sterile container outside the patient prior to placement at the wound site, a myriad of clot performance enhancing possibilities are allowed which would otherwise be difficult or barred from practice if they had to be performed in the patient's body at the wound site. With such an expanded capability to manipulate the blood fluid, it is believed dramatic improvements may be realized in clot formation control, efficacy, reliability, safety, cost performance; anticoagulant inhibition control, efficacy, reliability, safety, cost performance; anticlot inhibition control, efficacy, reliability, safety, cost performance; and general apparatus ergonomic user friendliness, efficacy, reliability, safety, cost performance, and the like, should be attainable.

These and various other advantages and features of novelty that characterize the present invention are pointed out with particularity in the claims annexed hereto informing a part hereof. However, for a better understanding of the present invention, its advantages and other objects obtained by its use, reference should be made to the drawings, which form a further part hereof and to the accompanying descriptive matter, in which there is illustrated and described preferred embodiments of the present invention.

BRIEF DESCRIPTION OF THE DRAWINGS

The invention will be further described in connection with the accompanying drawings, in which.

DETAILED DESCRIPTION OF THE PREFERRED EMBODIMENTS

Figure 1:
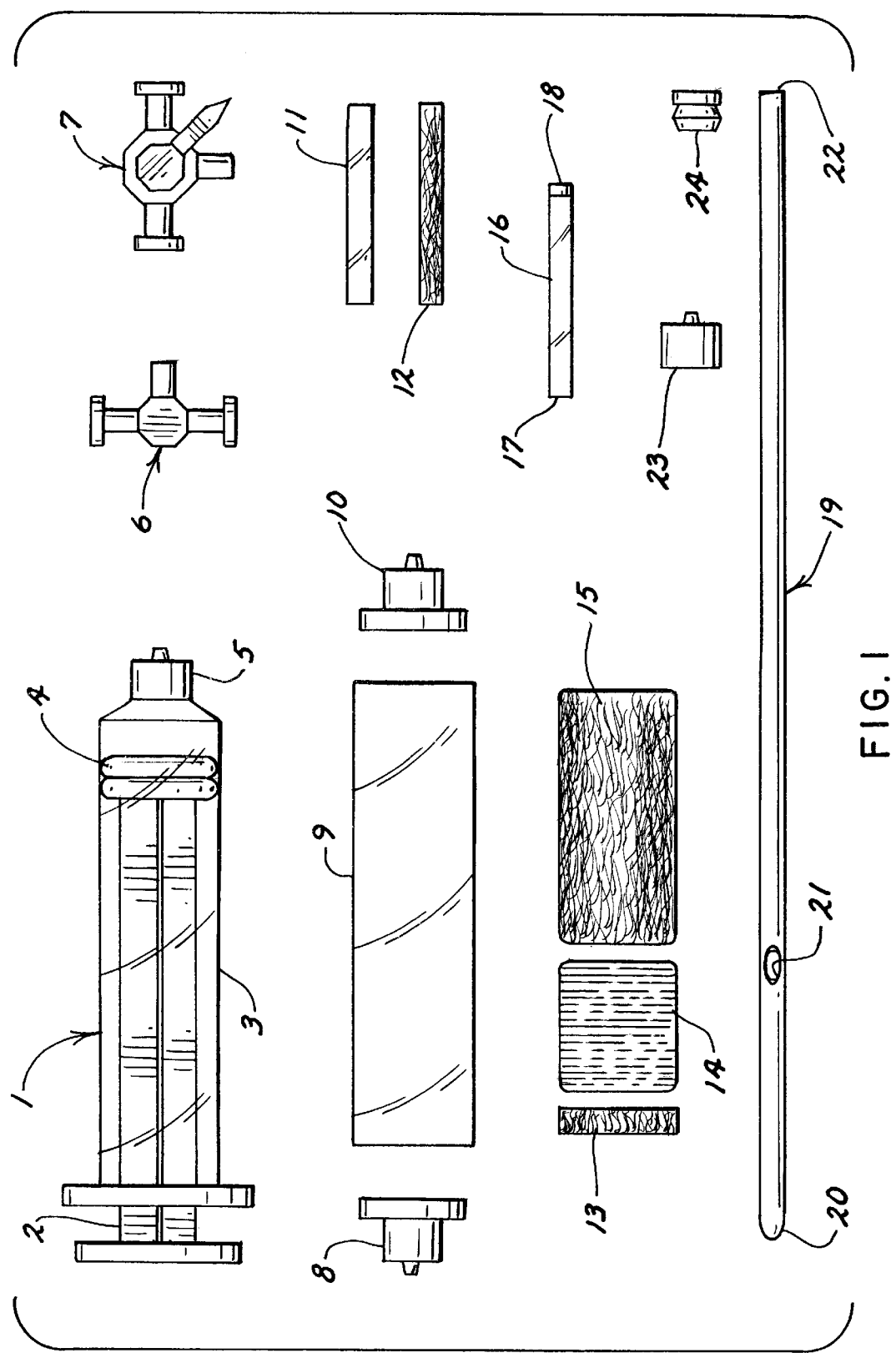
FIG. 1 is a mosaic pictorial of example apparatus components.

As used herein, the following terms have the following meanings: "Blood fluid" means a fluid containing natural components of whole blood, whether derived from whole blood, whole blood extracts, or products of ex vivo cell cultures, the blood fluid containing sufficient blood components to enable a portion of the blood fluid to clot subsequent to the initiation of a clotting cascade; "Clotting cascade(s)" means those chemical reactions occurring in blood which result in clot formation; "Clot" means a solidified mass of blood fluid having at least 90% of the available fibrin polymer cross-linked; "Biocompatible" means an agent is regarded by the regulating government body to be acceptable for implant in the human body; "Procoagulant" means a component capable of causing the blood fluid to form a clot; "Anticoagulant" means a component capable of preventing blood fluid clot formation; "Homogenous clot activation" means the blood fluid volume begins to form clot at substantially the same time and rate throughout its volume; and "Anticlot" means any of the naturally occurring blood fluid components which play a role in dissolution of a fibrin clot. All patents, patent applications, and references cited herewithin are hereby incorporated by reference.

The current invention concerns a novel method and apparatus for use in hemostatic closure of tissue wounds. The invention activates the clotting cascade of the blood fluid then transports the treated blood fluid in the wound in the patient such that the blood fluid can come into contact with the patient proximate the wound such that a clot is formed in the wound which prevents fluid from passing through the wound. The invention provides the opportunity to manipulate the blood fluid in respects needed to achieve the desired clot formation in the wound. This typically includes the elements of basic clot formation, including but not limited to, converting fibrinogen to a fibrin monomer then fibrin polymer which ultimately becomes a cross-linked fibrin polymer; control of anticoagulants including, but not limited to, heparin and Coumadin; and ultimately control of dissolution of the fibrin clot involving, but not limited to, serine proteases. By containing blood fluid to be used in wound clot formation and activating the clotting cascade under controlled sterile conditions outside the patient, the present invention method and apparatus provides the opportunity to manipulate the blood fluid used to term wound clot in many ways not before possible.

An apparatus to be used for sterile enclosed containment of the blood fluid may exist in many forms. A representative example of such enclosures would include syringes, cartridges, vials, test tubes, jars, bags, balloons, pouches, trays, dishes, bowls, tubing, catheters, cannula in general, and the like. A common feature to such containers would include the ability to keep the container substantially enclosed thereby preventing a level of contamination or loss of sterility unacceptable to the user. In practice, one or more containers may used separately or in combination. For example, a syringe connected to a catheter may be regarded as two containers or a single container with a transfer means, depending on the context of the discussion it is used in. Both context are acceptable and not intended to be limiting. Likewise, a single container may have one or more chambers internal to it. As a result, a single container with multiple chambers may be referred to as a single container or multiple containers. Again, both referrals are acceptable and should be interpreted in the context of the discussion and not be interpreted as to be limiting.

Generally, the containers have at least one fluid communication element associated with it which connects the inside to the outside of the container. A fluid communication element may have a normally open hole such as a luer fitting, a normally closed hole such as a septum, or a selective opening such as a molecular sieve or semipermeable membrane, and the like.

Procoagulant refers to any element or activity causing the blood fluid to form a clot. Procoagulants may be any such acting material, combination of materials, or mechanical activity. Mechanical procoagulant activities include mechanically stressing the blood fluid through blood fluid agitation, thermal induction, lysis, and the like. Procoagulant materials include those of biological origin such as cotton, thrombin, and the like. Procoagulant materials further include inorganic materials like glass and the like. Procoagulant materials additionally include synthetic organic materials like aminocaproic acid and the like, or polymers like dacron, nylon, polypropylene, silicone, and the like. Procoagulants may be used singularly or in combination.

Procoagulants, as with anticoagulant inhibitors and anticlot inhibitors discussed further on, may exist as an integral function of some other component, a coating on some other component, or be contained in some other component. Using procoagulants for illustrative purposes, an integral function example would be a glass walled container and the like. Glass causes the blood fluid to start clot formation while it also serves the functions of maintaining containment and sterility of the blood fluid. A coating example would be a static mixer having a surface bonded with diatomaceous earth and the like. An example of procoagulant containment in some other component may be either the presence of cotton loose within a container, the holding of thrombin in at least one chamber of multiple chambers in a container, or a container within another container, such as an inner sealed breakable vial containing aminocaproic acid, an inner container made from porous microbeads infused with aminocaproic acid, and the like.

Procoagulants, anticoagulant inhibitors, anticlot inhibitors and the like, may be added at the time of use, either before, during, or after and either singularly, sequentially, or in any combination with each other or with the blood fluid. Depending on the phase state of the material—gaseous, liquid, or solid, those skilled in the art can combine known hardware elements to implement the transfer.

As a preferred embodiment, the combining of procoagulant, anticoagulant inhibitor, anticlot inhibitor, and the like, either before, during, or after and either singularly, sequentially, or in any combination with blood fluid, preferably should be accomplished for homogenous respective functional results throughout the blood fluid. By example, a glass walled container can combine the functions of procoagulant, containment, and maintenance of sterility, however, unless the container is small, such as with a bundle of capillary-like tubes within a larger container, homogenous activation of the clotting cascade within the blood fluid does not occur. Specifically, a glass wall enclosing an undesirable large space would rapidly activate the clotting cascade of only that blood fluid close to the glass wall. Blood fluid at a distance from the wall reacts slower or not at all. The less than desirable result is that blood fluid at the glass wall forms a boundary layer of mature clot—that having substantial cross-linked fibrin polymer—which typically has little use because its adhesive capability and structure are often disrupted and destroyed during transport to the wound site. Likewise, the other zones of the blood fluid without clotting cascade activation do not clot in the wound site as desired. This clotting mechanism may be used but the aforementioned inferior results are to be expected, hence it is a preferred embodiment to provide ways to improve homogeneity of the desired blood fluid reaction. Apparatus examples accomplishing this include a static mixer, dynamic mixer, a porous matrix, and the like. Examples of a porous matrix include glass beads or cotton in a container—both provide a high surface area for intimate contact and turbulence within the blood fluid as it passes through the matrix. Thus, it may otherwise be stated that flowing blood fluid is preferred over pooled static blood and turbulent flow is preferred over laminar flow.

With regard to procoagulant, anticoagulant inhibitor, anticlot inhibitor and like materials, they may constitute more than one function, such as also making a static mixer, and the like, or they be separate as discussed above. This brings forth other embodiments and advantages of the invention. Specifically, it is also possible to classify procoagulant, anticoagulant inhibitor, anticlot inhibitor, and the like agents collectively as either catalytic or non-catalytic materials. By example, cotton is a catalytic material in the context that blood fluid is combined with it to initiate a reaction (procoagulation) in the blood fluid then it is separated, trace cotton fiber notwithstanding, and substantially retained from the blood fluid prior to returning the blood fluid to the wound site. To the contrary, the liquid drug protamine sulfate may be added to the blood fluid as a non-catalytic material, for example via an injection port septum on the enclosed sterile container, to initiate a reaction (inhibit the anticoagulant heparin) and stay with the blood fluid when it is returned to the wound site. By further example, diethylaminoethyl cellulose (DEAE), a catalytic material, may be held inside of a container via filtration methods and the like. When heparin anticoagulated blood fluid is added to the container, DEAE cellulose binds with the heparin removing it from the blood fluid thus keeping both the heparin and itself from returning to the wound site, trace presence remaining in blood fluid notwithstanding. In the interest of avoiding adverse patient outcomes, like an allergic response, it is a preferred embodiment of the present invention to not leave significant foreign materials in the blood fluid that is being returned to the wound site. As such, a benefit of the present invention is that by manipulating blood fluid to initiate the clotting cascade outside the patient, it is possible to use many more agents in catalytic form for procoagulation, anticoagulation inhibition, anticlot inhibition, and the like, than would be allowed if the selection was limited to agents that had to be biocompatible, e.g., approved for implant in the body. This increased selection allows for reduction or elimination of compromises in product efficacy, reliability, and safety. Further, even when working with non-catalytic implantable agents, the invention has new benefits such as the ability to ensure appropriate blood fluid mixing, concentration, clot volume and the like when performed outside the body.

Anticoagulant inhibitor is used to prevent any clot inhibiting agents present in the blood fluid from performing their function. An anticoagulant inhibitor may be specific or general in function. By example, thrombin acts as a procoagulant but can serve double 15 duty as an anticoagulant inhibitor simply by being present in volumes large enough to overwhelm the volume of anticoagulant present in the blood fluid. With the exception of protein deficiencies associated with hemophilia, anticoagulation typically occurs as the result of adding a foreign agent to the blood. Such agents typically include heparin and Coumadin. In catalytic form, polymers of selective electrical charge, diethylaminoethyl cellulose, and the like, may be placed in the blood fluid, singularly or in combination with an anticoagulant inhibiting drug and the like, to attract and hold an anticoagulant. In the non-catalytic form, protamine sulfate and the like may be used to render inactive a drug like heparin. Examples and the preferred manner and form of introduction have been discussed above.

Anticlot inhibitor is a term used to describe anything that impairs the function of fibrin clot degradation. Degradation of fibrin clots is naturally a function of plasmin, a serine protease that circulates as the inactive proenzyme, plasminogen. Anticlot inhibitors thus may serve in one way to disrupt the function of plasmin, plasminogen, and the like. Anticlot inhibitors may have value in extending the life of a wound sealing clot if desired. Examples of such inhibitors would be tranexamic acid, plasminogen binding material (PBM) available from Bioforma Research & Consulting, Inc., and the like. They may be applied in substantially the same way as discussed for anticoagulant inhibitors and procoagulants. Examples of the preferred manner and form of introduction have been discussed above.

The preferred embodiments of the apparatus of the present invention may be highly varied and is typically dependent on the individual application considering clinical situation, physician preference, and the like. As such, a clinical situation is selected and physician preference stated here for purposes of providing an illustrative example of one form of the invention apparatus. Presentation of this scenario is intended to be an instructive example of how the invention may be adapted to individual needs and should not be interpreted in a limited context as to how the invention applies. When used as a reference, those skilled in the art will be able to alter configurations and attributes of the apparatus to the same and other needs without departing from the scope and spirit of the present invention. The present example selected is that of post-introducer arterial wound closure following an angiographic procedure and the like. Post-introducer arterial wound closure typically involves the closure of a wound within a arterial wall such as the femoral artery, radial artery, and the like. Such wounds are typically subcutaneous in the sense that the artery is covered by tissue rather than being exposed by cut down through the tissue until the artery is visible to the practitioner. In the present illustration, an apparatus in configured for use typically with autologous whole blood.

FIG. 1 shows a typical array of components required to practice the invention when used to hemostatically close a post-introducer arterial wound. An advantage of the present invention apparatus example is that the components used are with rare exception standard off-the-shelf components commonly used throughout the medical industry and recognizable to those skilled in the art. A polymer 12 cc syringe 1 consisting of a plunger rod 2 connected to a fluid sealing piston 4 is slidingly placed within a cylinder 3 thereby allowing the cylinder to receive and expel fluids and the like through the distal port 5 of the syringe 1. A three-way connector 6 permits fluid communication between its three ports. A three-way valve connector 7 permits selective fluid communication between its three ports. Luer lock cylinder cap fittings 8 and 10, typically made of polycarbonate, are used to form a container when assembled to the ends of cylinder 9, also typically made of polycarbonate. Tubing section 11 represents a short section of substantially clear tubing typically made from the polymer polypropylene and the like. A porous material 12 typically made from cotton, open cell polyurethane, and the like will be used as a component in the fabrication of a bacteria resistant air vent. The porous materials of 13 and 15 represent both filtration and procoagulant materials and are typically both made of cotton and the like and typically resemble a cotton-ball consistency. Item 14 represents the anticoagulant binding material diethylaminoethyl (DEAE) cellulose. Item 16 represents the construct of a simple pulsitile indicator consisting of a substantially clear tube typically made of a polymer and having one end open 17 and the opposing end 18 closed either by addition of a plug or a melting and the like of the tube material. Tube 19 represents a length of tubing made of polyethylene and the like which will be used as a catheter. The outer diameter of tube 19 is typically the same french size as that specified for the introducer with which it is intended to be used. The distal end 20 is closed to fluid flow and forms an atraumatic tip for placement in an artery. The port 21 is proximal to the distal end 20 by typically 4 cm and typically approximates two-thirds the inner diameter of the tube and is placed through one wall of the tube 19 thereby permitting fluid communication between the outside of the tube with the inside of the tube extending fully to the proximal end 20 of tube 19. Item 23 represents a mating connector for assembly to and use with the proximal end 20 of tube 19 and at least one open port of the three-way connector 6. Item 24 represents a snap collar intended to be slidingly placed over tube 19 and bonded to the outside of tube 19 along its length between port 21 and proximal end 22. The contour of the snap fit of collar 24 is configured to connect with any one of several different brands of manufacture of introducer, an example of which is illustrated in FIG. 3.

Figure 2:
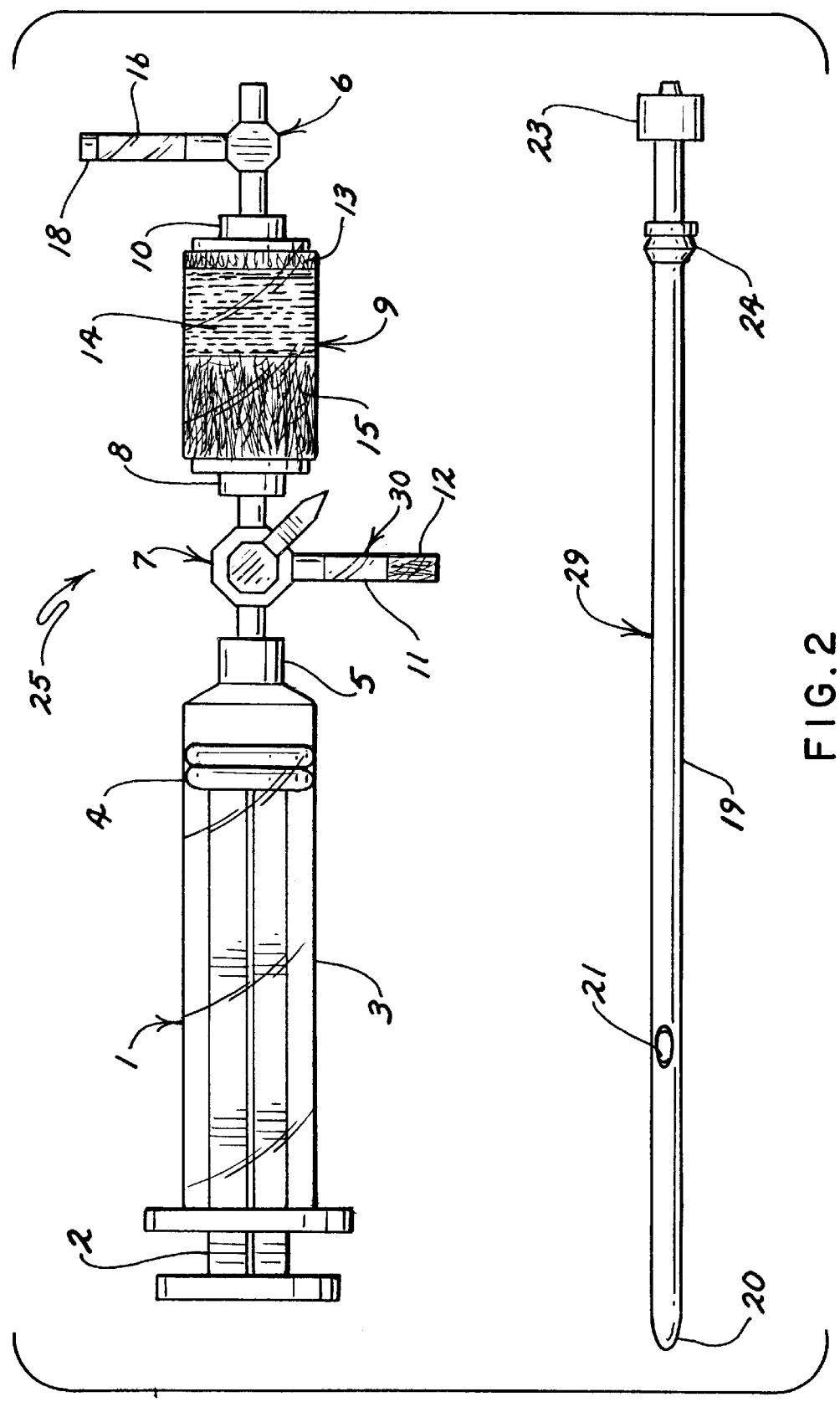
FIG. 2 is a pictorial view of the two principal apparatus component assemblies used for illustration.

FIG. 2 represents a typical assembly of the subcomponents in FIG. 1 into a blood fluid processor 25 and a blood fluid transfer catheter 29. The assembly 25 represents the three-way connector 6 attached to open end of the pulsitile indicator 16 and distal end of the assembly of either cylinder cap fittings 8 or 10 from FIG. 1 as fitted to the cylinder 9 of FIG. 1 therein containing distally the cotton material 13, medially the diethylaminoethyl cellulose material 14, and proximally the cotton material 15. The function of the cotton material 13 is primarily that of a filter which is used to retain the loose fibrous diethylaminoethyl (DEAE) cellulose material 14. The DEAE cellulose material serves to bind with and retain the anticoagulant, heparin, in the blood fluid to be used. The function of the cotton material 15 is to serve as a filter to retain the DEAE cellulose and also as a procoagulant of the blood fluid. Item 30 represents the construct of a bacteria resistant air vent. Item 12 from FIG. 1 placed in the distal end of tube 11 from FIG. 1. The proximal end of item 30 is attached to one port of the three-way valve 7 of FIG. 1 which in-turn mates the syringe port 5 of FIG. 1 with the proximal end cap connector 8 of FIG. 1 which is part of the aforementioned assembly containing the cotton and DEAE. The item of 29 represents the completed catheter assembly discussed above.

Figure 3:
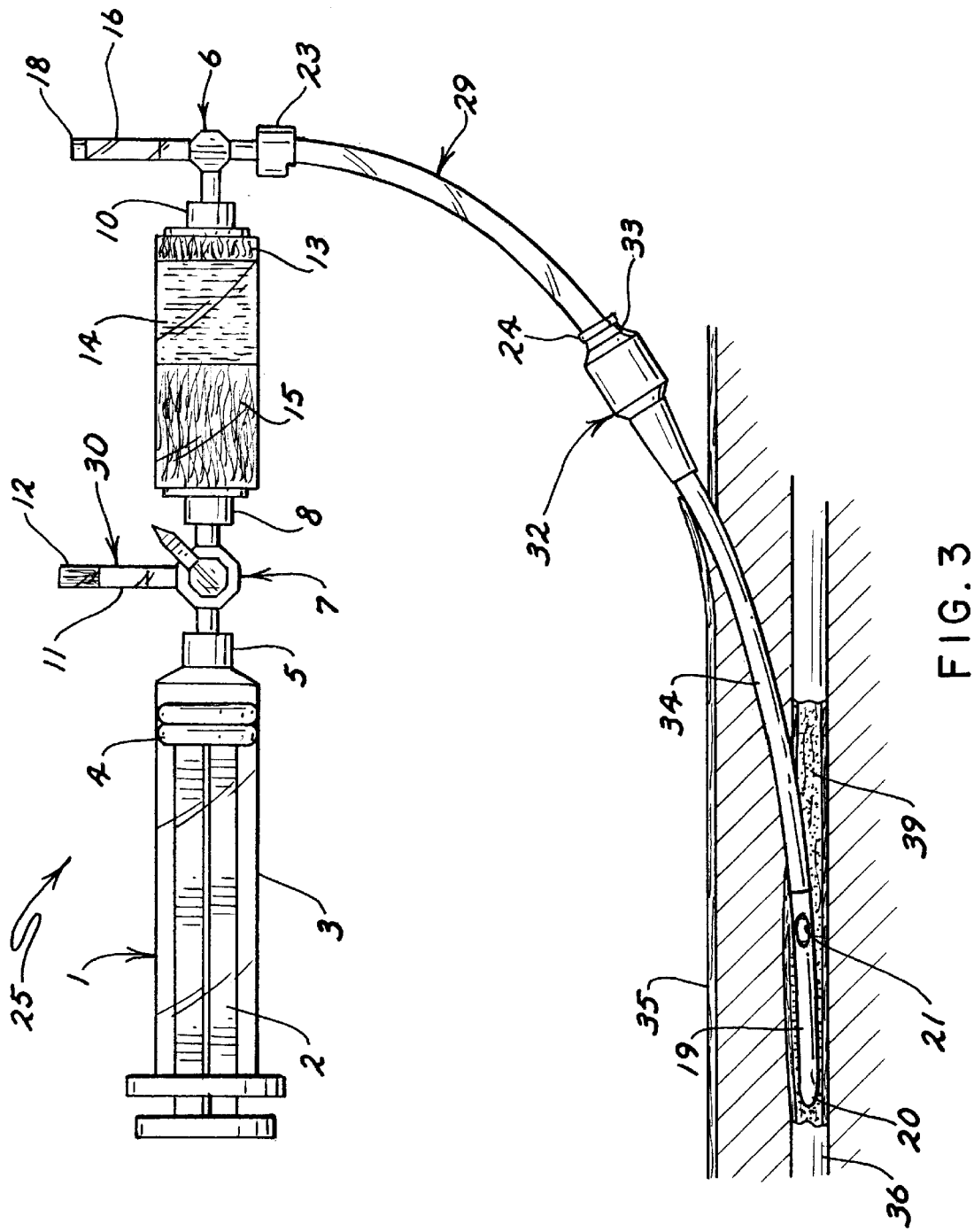
FIG. 3 is a pictorial of the assembled apparatus example as it is positioned initially in a patient.

FIG. 3 represents the completed apparatus assembly in-place within the introducer and patient as it would typically be used. Catheter 29 is shows placed through the introducer 32 with proximal end 33 snap fitted to the catheter and extending beyond the distal end 34 until port 21 is in fluid communication with the inside of artery 36 which is substantially enclosed within living tissue 35. Accordingly, blood fluid flows through port 21 up through catheter 29 and into the pulsitile indicator 16 and the containing apparatus assembly 31. The arterial systolic/diastolic pressure variation causes blood fluid within the pulsitile indicator 16 to vary compression of the entrapped air space within 16 thus providing positive indication of the presence of port 21 within the artery. The three-way valve of 31 is turned to permit withdrawal of the syringe plunger thereby encouraging blood fluid to flow through the cotton and DEAE cellulose. As this occurs trapped air within the syringe may be exhausted by switching the three valve to the exhaust side and advancing the plunger. Once substantially exhausted of air, the three-way valve is returned to the position which permits blood fluid to enter the syringe upon withdrawal of the plunger. As blood fluid flows through the apparatus toward the accumulating syringe, DEAE binds with and removes heparin from the blood fluid and the cotton present causes activation of the clotting cascade within the blood fluid as it passes through the cotton on its way to the accumulating syringe.

Figure 4:
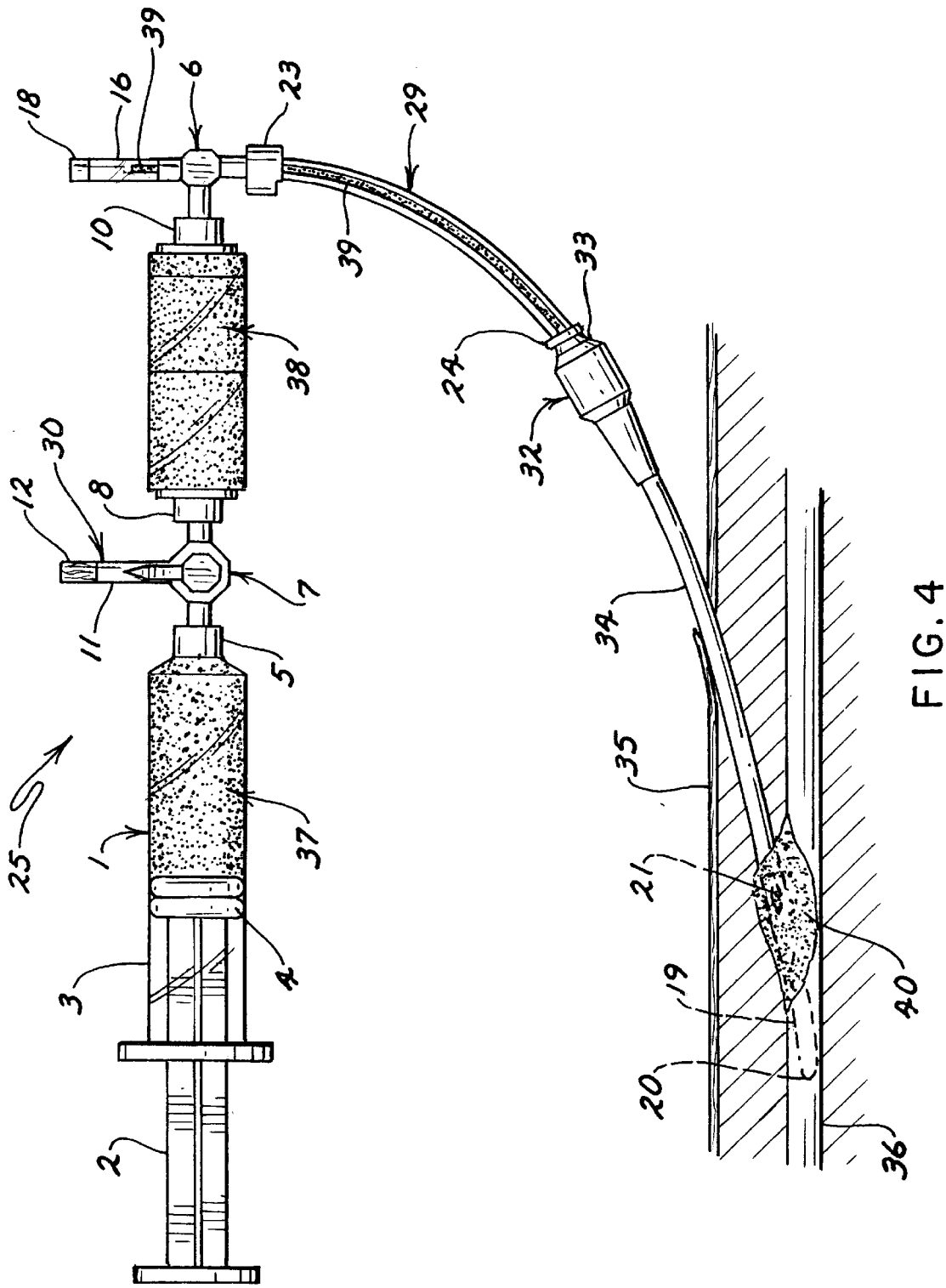
FIG. 4 is a pictorial of a method and apparatus example as positioned for return of blood fluid.

FIG. 4 represents the placement of blood fluid having an activated clotting cascade at the wound site. Both the catheter and introducer are withdrawn from the patient until there is a cessation of movement within the blood fluid 39 within the pulsitile indicator thus indicating that the catheter's distal port is now outside the artery. Once this has been established, the syringe plunger is advanced thereby driving clot-activated blood fluid 40 out the distal catheter port and depositing it about the wound where clotting continues. As the blood fluid 40 continues to advance to a mature clot, proximal pressure is applied to the artery and both the introducer and catheter are fully removed from the patient. After typically 3 to 5 minutes, proximal direct pressure may be eliminated and the procedure considered complete. Although not presented in this example, anticlot inhibition may have also been used if desired as previously discussed. Those skilled in the art will observe that blood fluid between the distal catheter port and the DEAE cellulose material escaped removal of anticoagulant. Experimentation has shown that such residual anticoagulant does not inhibit clot formation in the considerable larger volume of activated blood fluid. However, if this were a problem, it certainly would be possible to have a closed loop apparatus so that blood fluid does not travel the same fluid communication conduit to and from the wound area. Alternatively, an anticoagulant inhibitor may be placed within the catheter starting at the distal port and extend all the way back through to the proximal end of the device if desired. These alternatives merely illustrate examples of the tremendous latitude available to a product designer within the present invention.

In providing the user with a functional construct of the present invention, it may be desirable to provide the user with a kit of components bundled together for ease of use. As with other aspects of the invention illustrated earlier, this invention aspect can take many forms and is typically dependent on clinical application, user preferences, and the like. As such, the following is merely an illustrative example of what a kit may consist of and should not be interpreted as a limitation of the present invention. For the sake of continuity with previous illustrations, this illustration will be in the context of a typical kit for use with minimally invasive angiographic procedures and the like. Thus, the kit may contain a wound closure apparatus of the present invention singularly or in combination with one or more of the following: an introducer, guidewire, dilator, obturator, collapsible catheter sheath, Seldinger needle, balloon catheter, infusion catheter, stent, scalpel, suture line, needle, pouch, tray, tray lid, instructions for use, adhesive identification label, sterility indicator, and the like.

It is to be understood, however, that even though numerous characteristics and advantages of the present invention have been set forth in the foregoing description, together with details of the structure and function of present invention, the sequence or order of the specific steps, or the actual compositions or materials used may vary somewhat. Furthermore, it will be appreciated that this disclosure is illustrative only and that changes may be made in detail, especially in matters of shape, size, arrangement of parts or sequence or elements of aspects of the invention within the principles of the invention to the full extent indicated by the broad general meaning of the terms in which the appended claims, which form a further part hereof, are expressed.

What is claimed is:

1. A method of closing a wound in a patient, the method comprising the steps of:
    a) treating a blood fluid with a procoagulating, agent to initiate a clotting cascade during a first time period such that at least a portion of the blood fluid will form a clot of blood during a second time period subsequent to the first time period, the blood fluid containing sufficient blood components to enable a portion of the blood fluid to clot during the second time period subsequent to the initiation of the clotting cascade during the first time period; the blood fluid being whole blood; and
    b) transporting the treated blood fluid to the wound in the patient such that the blood fluid comes into contact with the patient proximate the wound and the clotting cascade comes generally to a conclusion and a clot forms proximate the wound such that the clot prevents fluid from passing through the wound.

2. The method of claim 1, the step of treating the blood fluid including (1) providing a containment chamber in which the blood fluid can be contained; (2) placing the blood fluid in the containment chamber; and (3) initiating the clotting cascade by exposing the blood fluid to a procoagulating agent within the containment chamber.

3. The method of claim 2, the step of treating the blood fluid including providing a substantially enclosed sterile containment chamber, the chamber containing a procoagulating agent.

4. The method of claim 3, wherein the procoagulating agent is a porous matrix and the step of treating the blood fluid includes passing the blood fluid through the porous matrix.

5. The method of claim 4, wherein the porous matrix is biological in origin and the step of treating the blood fluid includes exposing the blood fluid to the biologic material such that the clotting cascade is initiated within the blood fluid.

6. The method of claim 5, wherein the biologic material is a biologic agent is cotton, diatomaceous earth.

7. The method of claim 4, wherein the porous matrix is an inorganic material and the step of treating the blood fluid includes exposing the blood fluid to the inorganic material such that the clotting cascade is initiated within the blood fluid.

8. The method of claim 7, wherein the inorganic material is glass.

9. The method of claim 4, wherein the porous matrix is a synthetic polymer and the step of treating the blood fluid includes exposing the blood fluid to the synthetic polymer such that the clotting cascade is initiated within the blood fluid.

10. The method of claim 9, wherein the synthetic polymer agent is a synthetic polymer selected from the group consisting of dacron, silicone, polyurethane, polycarbonate, polyethylene, polyvinylchloride, polypropylene and nylon.

11. The method of claim 1, further comprising the step of applying direct pressure to an artery proximal to a wound in the artery thereby reducing arterial blood pressure while clot forms in the wound.

12. The method of claim 1, further comprising the step of treating a blood fluid including treatment of the blood fluid with an anticoagulant inhibiting agent.

13. The method of claim 12, the step of treating a blood fluid further including treatment of the blood fluid with an anticlot inhibiting agent.

14. The method of claim 1, the step of treating a blood fluid including treatment of the blood fluid with an anticlot inhibiting agent.

15. A clotting cascade initiation apparatus within which a blood fluid can be received and retained, the blood fluid being useful for treatment of a wound within a patient, said apparatus comprising:
    a substantially enclosed sterile containment chamber within which the blood fluid can be received and retained,
the substantially enclosed sterile containment chamber containing a procoagulating agent; and a cannulated delivery member in fluid communication with the containment chamber such that blood fluid can pass out of the containment chamber and through the cannulated delivery member; wherein a clotting cascade is initiated when the blood fluid is received in the sterile containment chamber and exposed to the procoagulating agent within the chamber, and subsequently delivered via the cannulated delivery member to the wound subsequent to the initiation of the clotting cascade, such that the clotting cascade, initiated within the sterile containment chamber prior to the delivery of the blood fluid to the wound, can be completed within the wound and a clot can form within the wound when the clotting cascade is completed.

16. The clotting cascade initiation apparatus of claim 15, further including a cannula for delivering blood fluid to the wound, the cannula being in communication with the containment chamber.

17. The clotting cascade initiation apparatus of claim 15, further including a cannula for withdrawing blood fluid from the patient and delivering blood fluid to the wound, the cannula being in communication with the containment chamber.

18. The clotting cascade initiation apparatus of claim 15, wherein the procoagulating agent is a porous matrix through which the blood fluid can be passed.

19. The clotting cascade initiation apparatus of claim 18, wherein the porous matrix is an inorganic material.

20. The clotting cascade initiation apparatus of claim 19, wherein the inorganic material is glass.

21. The clotting cascade initiation apparatus of claim 18, wherein the porous matrix is a synthetic polymer.

22. The clotting cascade initiation apparatus of claim 21, wherein the synthetic polymer is a synthetic polymer selected from the group consisting of dacron, silicone, polyurethane, polycarbonate, polyethylene, polyvinylchloride, polypropylene and nylon.

23. The clotting cascade initiation apparatus of claim 18, wherein the porous matrix is biological in origin.

24. The clotting cascade initiation apparatus of claim 23, wherein the biologic material is a biologic material selected from the group consisting of cotton, diatomaceous earth.

25. A method of closing a wound in a patient, said method comprising the steps of:
   a) providing a clotting cascade initiation apparatus within which a blood fluid can be received, said apparatus including a substantially enclosed sterile containment chamber within which the blood fluid can be received and retained, and a cannulated delivery member in fluid communication with the containment chamber; the containment chamber containing a procoagulating agent; wherein a clotting cascade can be initiated when the blood fluid is placed into the sterile containment chamber and thereby exposed to the procoagulating agent;
   b) placing a sufficient amount of blood fluid into the containment chamber to provide a sufficient amount of blood fluid to enable the blood fluid to knit together to form a clot proximate the wound once the clotting cascade is initiated; and
   c) delivering the blood fluid to the wound via the cannulated delivery member subsequent to the initiation of the clotting cascade in the containment chamber such that the clotting cascade can be completed and a clot can form within the wound after the blood fluid is delivered to the wound.

26. The method of closing a wound in a patient of claim 25, wherein the procoagulating agent is a porous matrix and the step of placing the blood fluid in the chamber includes passing the blood fluid through the porous matrix.

27. The method of closing a wound in a patient of claim 25, wherein the procoagulating agent is biological in origin.

28. The method of closing a wound in a patient of claim 27, wherein the biologic material is a biologic material selected from the group consisting of cotton, diatomaceous earth.

29. The method of closing a wound in a patient of claim 25, wherein the procoagulating agent is inorganic.

30. The method of closing a wound in a patient of claim 29, wherein the inorganic agent is glass.

31. The method of closing a wound in a patient of claim 25, wherein the procoagulating agent is a synthetic polymer.

32. The method of closing a wound in a patient of claim 31, wherein the synthetic polymer is a synthetic polymer selected from the group consisting of dacron, silicone, polyurethane, polycarbonate, polyethylene, polyvinylchloride, polypropylene and nylon.

33. The method of claim 15, further comprising the step of applying direct pressure to an artery proximal to a wound in the artery thereby reducing arterial blood pressure while clot forms in the wound.

34. A method of closing a wound in a patient, said method comprising the steps of:
   a) providing a clotting cascade initiation apparatus within which a blood fluid can be received and a clotting cascade can be initiated, said apparatus including a substantially enclosed sterile containment chamber within which the blood fluid can be received and retained;
   b) placing a sufficient amount of blood fluid into the containment chamber to provide a sufficient amount of blood fluid to enable the blood fluid to knit together to form a clot once the clotting cascade is initiated, the blood fluid being whole blood;
   c) placing a procoagulating agent within the substantially enclosed sterile containment chamber such that the procoagulating agent comes into contact with the blood fluid and a clotting cascade is initiated in blood fluid; and
   d) delivering the blood fluid to the wound subsequent to the initiation of the clotting cascade in the containment chamber such that the clotting cascade can be completed and a clot can form within the wound.

35. The method of closing a wound in a patient of claim 34, wherein the step of placing the procoagulating agent within the substantially enclosed sterile containment chamber includes placing a biocompatible procoagulating agent within the chamber such that the procoagulating agent is mixed with the blood fluid.

36. The method of closing a wound in a patient of claim 35, wherein the biocompatible procoagulating agent is a biological material.

37. The method of closing a wound in a patient of claim 36, wherein the biological material is a biocompatible procoagulating agent selected from the group consisting of thrombin, collagen, fibrin and fibrinogen.

38. The method of closing a wound in a patient claim 35, wherein the biocompatible procoagulating agent is a synthetic compound.

39. The method of closing a wound in a patient of claim 38, wherein the synthetic biocompatible procoagulating agent is aminocaproic acid.

40. The method of closing a wound in a patient of claim 35, wherein the biocompatible procoagulating agent is an inorganic compound.

41. The method of closing a wound in a patient of claim 35, wherein the inorganic biocompatible procoagulating agent is a salt.

42. A method of closing a wound in a patient, said method comprising the steps of:
   a) providing a clotting cascade initiation apparatus within which a blood fluid can be received and a clotting cascade can be initiated, said apparatus including a substantially enclosed sterile containment chamber within which the blood fluid can be received and retained;
   b) placing a sufficient amount of blood fluid into the containment chamber to provide a sufficient amount of blood fluid to enable the blood fluid to knit together to form a clot once the clotting cascade is initiated, the blood fluid being whole blood;
   c) mechanically stressing the blood fluid within the substantially enclosed sterile containment chamber such that a clotting cascade is initiated in blood fluid, and d) delivering the blood fluid to the wound subsequent to the initiation of the clotting cascade in the containment chamber such that the clotting cascade can be completed and a clot can form within the wound.

43. The method of closing a wound in a patient of claim 42, wherein the step of mechanically stressing the blood fluid within the substantially enclosed sterile containment chamber is selected from the group consisting of blood fluid agitation, thermal induction and lysis.

44. A method of closing a wound in a patient, said method comprising the steps of:
   a) providing a clotting cascade initiation apparatus within which a blood fluid can be received, said apparatus including a substantially enclosed sterile containment chamber within which the blood fluid can be received and retained, and a cannulated delivery member in fluid communication with the containment chamber; the containment chamber containing a procoagulating agent; wherein a clotting cascade can be initiated when the blood fluid is placed into the sterile containment chamber and thereby exposed to the procoagulating agent;
   b) drawing a sufficient amount of an autologous blood fluid from the patient into the containment chamber to provide a sufficient amount of blood fluid to the wound, once the clotting cascade is initiated, to enable the blood fluid to knit together to form a clot, the blood fluid being whole blood; and
   c) delivering the blood fluid to the wound via the cannulated delivery member subsequent to the initiation of the clotting cascade in the containment chamber so that the clotting cascade can be completed and a clot can fonn within the wound after the blood fluid is delivered to the wound.

45. A clotting cascade initiation apparatus within which a blood fluid can be received and retained, the blood fluid being useful for treatment of a wound within a patient, said apparatus comprising:
   a substantially enclosed sterile containment chamber within which the blood fluid can be received and retained, the substantially enclosed sterile containment chamber containing a procoagulating agent; and a cannulated delivery member in fluid communication with the containment chamber such that blood fluid can pass out of the containment chamber and through the cannulated delivery member; wherein a clotting cascade is initiated when the blood fluid is accepted into the sterile containment chamber and exposed to the procoagulating agent within the chamber, and the blood fluid can be delivered to the wound subsequent to the initiation of the clotting cascade via the cannulated delivery member such that the clotting cascade can be completed proximate the wound and a clot can form proximate the wound when the clotting cascade is completed.

46. A method of closing wound in a patient the method consisting essentially of,
   (a) withdrawing an amount of blood fluid from the patient sufficient to form a clot within a wound of sufficient size to prevent fluid from passing through the wound, the blood fluid being whole blood;
   (b) exposing the blood fluid to a procoagulating agent to initiate a clotting cascade within the blood fluid; and
   (c) subsequently returning the blood fluid to the patient proximate the wound such that the blood fluid, in which the clotting cascade has been initiated, will subsequently clot proximate the wound such that fluid cannot pass through the wound.

47. The method of claim 46, wherein the step of exposing the blood fluid includes exposing the blood fluid to an anticoagulant inhibiting agent.

48. The methods of claims 46 and 47, wherein the step of exposing includes the step of exposing the blood fluid to an anticlot inhibiting agent.

49. The method of claim 47, wherein the anticoagulant inhibiting agent is an inhibiting agent selected from the group consisting of catalytic and non-catalytic inhibiting agents.

50. The method of claim 46, wherein the whole blood contains an anticoagulant.

51. A kit for closing a wound in a patient, the patient containing a blood fluid; said kit comprising a substantially enclosed sterile containment chamber within which the blood fluid can be received and retained, the substantially enclosed sterile containment chamber containing a procoagulating agent; wherein a clotting cascade is initiated when the blood fluid is accepted into the sterile containment chamber and exposed to the procoagulating agent within the chamber, and the blood fluid can be delivered to the wound subsequent to the initiation of the clotting cascade such that the clotting cascade can be completed within the wound and a clot can form proximate the wound when the clotting cascade is completed; and
   additional apparatus selected from the group consisting of an introducer, guidewire, dilator, obturator, collapsible catheter sheath, Seldinger needle, balloon catheter, infusion catheter, stent, scalpel, suture line, needle, pouch, tray, tray lid, instructions for use, adhesive identification label and sterility indicator.

52. The kit of claim 51; further comprising a cannulated delivery member in fluid communication with the containment chamber such that blood fluid can pass out of the containment chamber and through the camulated delivery member.

53. The kit of claim 52, wherein the substantially sterile containment chamber contains an agent selected from the group consisting of an anticoagulant inhibiting agent, an anticlot inhibiting agent and a combination thereof.

54. The apparatus of claim 15 or 45, the substantially enclosed sterile containment chamber further containing an anticoagulant inhibiting agent.

55. The apparatus of claim 54; the substantially enclosed sterile containment chamber further containing an anticlot inhibiting agent.

56. The apparatus of claim 54, wherein the anticoagulant inhibiting agent is an agent selected from the group consisting of catalytic agents and non-catalytic agents.

57. The apparatus of claim 15 or 45; the substantially enclosed sterile containment chamber further containing an anticlot inhibiting agent.

58. The apparatus of claim 15 or 45; constituting a kit when when further comprising additional apparatus selected from the group consisting of an introducer, guidewire, dilator, obturator, collapsible catheter sheath, Seldinger needle, balloon catheter, infusion catheter, stent, scalpel, suture line, needle, pouch, tray, tray lid, instructions for use, adhesive identification label and sterility indicator.

59. The method of claim 25, 34, 42, or 44, wherein the step of providing includes providing a substantially enclosed sterile containment chamber containing an anticoagulant inhibiting agent.

60. The methods of claim 25, 34, 42, or 44 wherein the step of providing includes providing a substantially enclosed sterile containment chamber containing an anticlot inhibiting agent.

* * * * *

UNITED STATES PATENT AND TRADEMARK OFFICE
CERTIFICATE OF CORRECTION

PATENT NO.    : 6,159,232
DATED         : December 12, 2000
INVENTOR(S)   : Karol L. Nowakowski It is certified that error appears in the above-identified patent and that said Letters Patent is hereby corrected as shown below:

Title page,
Following Item [22] insert:
  -- Related U.S. Application Data
[60]    Provisional Application No. 60/069,834, filed on Dec. 16, 1997. --

Column 1,
Line 20, delete "IS";

Column 2,
Line 19, delete "diseases" and insert therefor -- disease --;
Line 44, delete "the" and insert therefor -- a --;

Column 3,
Line 56, delete "Homogenous" and insert therefor -- Homogeneous --;

Column 4,
Line 16, delete "term" and insert therefor -- form --;

Column 5,
Line 25, delete "homogenous" and insert therefor -- homogeneous --;

Column 6,
Line 29, delete "15";

Column 7,
Line 56, delete "Item" and insert therefor -- hence --;

Column 8,
Line 3, after the first occurrence of the word "and" please insert -- the --;
Line 25, delete "shows" and insert therefor -- shown --;

Column 9,
Line 34, after the first occurrence of the word "details" please delete "of" and insert therefor -- so --;

Column 10,
Line 35, delete "further comprising";

Column 12,
Line 41, after the first occurrence of the word "patient" please insert -- of --;

UNITED STATES PATENT AND TRADEMARK OFFICE
CERTIFICATE OF CORRECTION

PATENT NO. : 6,159,232
DATED : December 12, 2000
INVENTOR(S) : Karol L. Nowakowski It is certified that error appears in the above-identified patent and that said Letters Patent is hereby corrected as shown below:

<u>Column 13,</u>
Line 32, delete "fonn" and insert therefor -- form --;
Line 55, after the first occurrence of the word "patient" please insert -- , --;
Line 56, after the first occurrence of the word "of" please delete "." and insert therefor -- : --;

<u>Column 14,</u>
Line 53, after the first occurrence of the word "when" please delete "when";

Signed and Sealed this

Twenty-first Day of October, 2003

JAMES E. ROGAN
*Director of the United States Patent and Trademark Office*